United States Patent

Schefczik et al.

[11] Patent Number: 5,612,465
[45] Date of Patent: Mar. 18, 1997

[54] PHENYLAZOTRIAZOLOPYRIDINE DYESTUFFS

[75] Inventors: Ernst Schefczik, Ludwigshafen; Ruediger Sens, Mannheim; Karl-Heinz Etzbach, Frankenthal; Helmut Reichelt, Neustadt; Clemens Grund, Mannheim, all of Germany

[73] Assignee: BASF Aktiengesellschaft, Ludwigshafen, Germany

[21] Appl. No.: 592,310

[22] PCT Filed: Aug. 9, 1994

[86] PCT No.: PCT/EP94/02634

§ 371 Date: Feb. 12, 1996

§ 102(e) Date: Feb. 12, 1996

[87] PCT Pub. No.: WO95/05420

PCT Pub. Date: Feb. 23, 1995

[30] Foreign Application Priority Data

Aug. 13, 1993 [DE] Germany .......................... 43 27 222.3

[51] Int. Cl.⁶ .......................... C09B 29/36; C07D 471/04
[52] U.S. Cl. .......................... 534/752; 546/119
[58] Field of Search .......................... 534/752; 546/119

[56] References Cited

U.S. PATENT DOCUMENTS 5,101,028 3/1992 Schefczik et al. .................. 546/119 X

FOREIGN PATENT DOCUMENTS

| 413226 | 2/1991 | European Pat. Off. ............... 546/119 |
| 4020768 | 1/1992 | Germany .............................. 534/752 |
| 95/04733 | 2/1995 | WIPO ................................. 546/119 |

*Primary Examiner*—Fiona T. Powers
*Attorney, Agent, or Firm*—Oblon, Spivak, McClelland, Maier & Neustadt, P.C.

[57] ABSTRACT

Azo dyestuffs of the formula

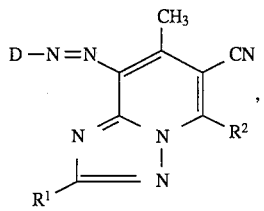

where
  $R^1$ is unsubstituted or substituted $C_1$–$C_{20}$-alkyl, unsubstituted or substituted phenyl, or unsubstituted or substituted mercapto,
  $R^2$ is hydroxyl or mercapto and
  D is the radical of a diazo component which is selected from the group consisting of the radicals of the formulae

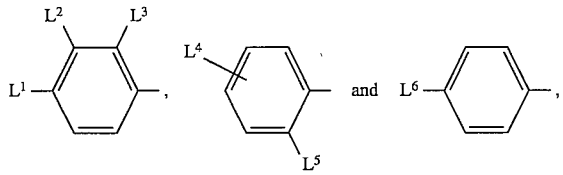

where $L^1$ is $C_1$–$C_4$-alkyl, unsubstituted or substituted $C_1$–$C_4$-alkoxy or unsubstituted or substituted amino, one of the two radicals $L^2$ and $L^3$ is hydrogen and the other is $C_1$–$C_4$-alkyl, unsubstituted or substituted $C_1$–$C_4$-alkoxy or unsubstituted or substituted amino, $L^4$ is hydrogen or $C_1$–$C_4$-alkyl, $L^5$ is unsubstituted or substituted $C_1$–$C_4$-alkoxy or $C_1$–$C_4$-alkylthio and $L^6$ is unsubstituted or substituted $C_8$–$C_{13}$-alkyl or phenoxy, their use for dyeing or printing textile materials and novel mercaptotriazolopyridines are described.

5 Claims, No Drawings

PHENYLAZOTRIAZOLOPYRIDINE DYESTUFFS

This application is a 371 of PCT/EP94/02634 filed Aug. 9, 1994.

The present invention relates to novel azo dyestuffs of the formula I

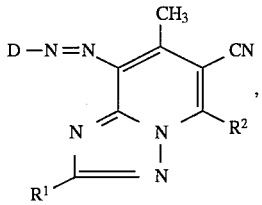

where
$R^1$ is $C_1$–$C_{20}$-alkyl which is unsubstituted or substituted and can be interrupted by 1 to 4 ether oxygen atoms, or is unsubstituted or substituted phenyl, or mercapto or unsubstituted or substituted alkylthio, $R^2$ is hydroxyl or mercapto and D is the radical of a diazo component which is selected from the group consisting of the radicals of the formulae

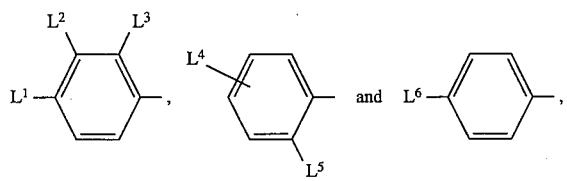

where $L^1$ is $C_1$–$C_4$-alkyl, $C_1$–$C_4$-alkoxy which is unsubstituted or substituted by $C_1$–$C_4$-alkoxy, or is $C_1$–$C_4$-alkanoylamino, $C_1$–$C_4$-alkylsulfonylamino or a radical of the formula $NY^1Y^2$, where $Y^1$ and $Y^2$ independently of one another in each case are hydrogen or $C_1$–$C_4$-alkyl or, together with the nitrogen bonding them, are a 5- or 6-membered saturated heterocyclic radical, one of the two radicals $L^2$ and $L^3$ is hydrogen and the other is $C_1$–$C_4$-alkyl, $C_1$–$C_4$-alkoxy which is unsubstituted or substituted by $C_1$–$C_4$-alkoxy, or is $C_1$–$C_4$-alkanoylamino, $C_1$–$C_4$-alkylsulfonylamino or a radical of the formula $NY^1Y^2$, in which $Y^1$ and $Y^2$ in each case have the abovementioned meanings, $L^4$ is hydrogen or $C_1$–$C_4$-alkyl, $L^5$ is $C_1$–$C_4$-alkoxy which is unsubstituted or substituted by $C_1$–$C_4$-alkoxy, or is $C_1$–$C_4$-alkylthio and $L^6$ is $C_8$–$C_{13}$-alkyl which can be interrupted by 1 to 4 ether oxygen atoms, or is phenoxy, to their use for dyeing or printing textile materials and to novel mercaptotriazolopyridines.

Triazolopyridine azo dyestuffs containing diazo components from the aniline series have already been disclosed in DE-A-4 020 768. However, it has been shown that the dyestuffs described there still have applicational deficiencies.

It is an object of the present invention to make available novel azo dyestuffs containing a coupling component from the triazolopyridine series and a diazo component from the aniline series and which have a high fastness to dry heat and pleating, high brilliance and high dyeing power.

We have now found that this object can be achieved by the azo dyestuffs of the formula I described in greater detail at the beginning.

The dyestuffs of the formula I can occur in several tautomeric forms, which are all covered by the patent claims. For example, the dyestuffs can occur in the following tautomeric forms:

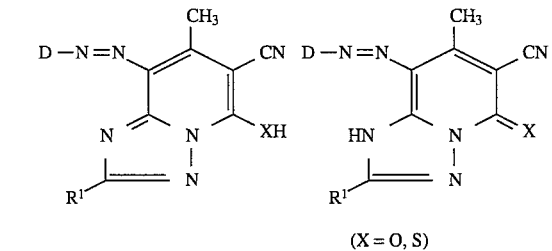

(X = O, S)

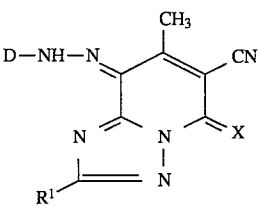

If $R^1$ in formula I is a substituted $C_1$–$C_{20}$-alkyl radical; suitable substituents can be eg. phenyl, phenoxy, carboxyl or $C_1$–$C_{20}$-alkoxycarbonyl whose alkyl chain can be interrupted by 1 to 4 ether oxygen atoms and is unsubstituted or substituted by phenyl or phenoxy. The alkyl radicals as a rule then have 1 or 2 substituents.

If in formula I alkyl radicals occur which are interrupted by ether oxygen atoms, those alkyl radicals are preferred which are interrupted by 1 or 2 ether oxygen atoms.

If in formula I substituted phenyl radicals occur, suitable substituents, if not stated otherwise, can be eg. $C_1$–$C_4$-alkyl, $C_1$–$C_4$-alkoxy, halogen, in this case in particular chlorine or bromine, cyano, nitro or carboxyl. The phenyl radicals as a rule then have 1 to 3 substituents.

If the radicals $Y^1$ and $Y^2$, together with the nitrogen bonding them, are a 5- or 6-membered saturated heterocyclic radical, suitable radicals for this purpose are eg. pyrrolidinyl, piperidinyl, morpholinyl, piperazinyl or N-($C_1$–$C_4$-alkyl)piperazinyl.

The radicals $R^1$, $L^1$, $L^2$, $L^3$, $L^4$, $Y^1$ and $Y^2$ are eg. methyl, ethyl, propyl, isopropyl, butyl, isobutyl or sec-butyl.

The radicals $R^1$ are furthermore eg. pentyl, isopentyl, neopentyl, tert-pentyl, hexyl, heptyl, 1-ethylpentyl, octyl, isooctyl, 2-ethylhexyl, nonyl, isononyl, decyl, isodecyl, undecyl, dodecyl, tridecyl, isotridecyl, tetradecyl, pentadecyl, hexadecyl, heptadecyl, octadecyl, nonadecyl, eicosyl (the above names isooctyl, isononyl, isodecyl and isotridecyl are trivial names and originate from the alcohols obtained by the oxo synthesis—cf. for this Ullmanns Enzyklopädie der technischen Chemie [Ullmann's Encyclopedia of Industrial Chemistry], 4th edition, volume 7, pages 215 to 217, and also volume 11, pages 435 and 436), 2-methoxyethyl, 2-ethoxyethyl, 2-propoxyethyl, 2-isopropoxyethyl, 2-butoxyethyl, 2- or 3-methoxypropyl, 2- or 3-ethoxypropyl, 2- or 3-propoxypropyl, 2- or 3-butoxypropyl, 2- or 4-methoxybutyl, 2- or 4-ethoxybutyl, 2- or 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- or 4-butoxybutyl, 4,8-dioxadecyl, 3,6,9-trioxadecyl, 3,6,9-trioxaundecyl, 3,6,9,12-tetraoxatridecyl, 3,6,9,12-tetraoxatetradecyl, 2-carboxyethyl, 2-methoxycarbonylethyl, benzyl, 1- or 2-phenylethyl, 2-, 3- or 4-methylbenzyl, 2-, 3- or 4-methoxybenzyl, 2-, 3- or 4-chlorobenzyl, 2-, 3- or 4-nitrobenzyl, 3-benzyloxypropyl, phenoxymethyl, 6-phenoxy-4-oxahexyl, 8-phenoxy-4-oxaoctyl, 2-, 3- or 4-methylphenyl, 2-, 3- or 4-methoxyphenyl, 2-, 3- or 4-chlorophenyl, 2-, 3- or 4-nitrophenyl, 2-, 3- or 4-carboxyphenyl, methylthio, ethylthio, propylthio, isopropylthio, butylthio, isobutylthio, sec-butylthio, pentylthio, isopentylthio, neopentylthio, tertpentylthio, hexylthio, heptylthio, 1-ethylpentylthio, octylthio, isooctylthio, 2-ethylhexylthio, nonylthio, isononylthio, decylthio, isodecylthio, undecylthio, dodecylthio, tridecylthio, isotridecylthio, tetradecylthio, pentadecylthio, hexadecylthio, heptadecylthio, octadecylthio, nonadecylthio or eicosylthio.

The radicals $L^1$, $L^2$, $L^3$ and $L^5$ are furthermore eg. methoxy, ethoxy, propoxy, isopropoxy, butoxy, isobutoxy, sec-butoxy, 2-methoxyethyl, 2-ethoxyethyl, 2-propoxyethyl, 2-butoxyethyl, 2- or 3-methoxypropyl, 2- or 3-ethoxypropyl, 2- or 3-propoxypropyl, 2- or 3-butoxypropyl, 2- or 4-methoxybutyl, 2- or 4-ethoxybutyl, 2- or 4-propoxybutyl or 2- or 4-butoxybutyl.

The radicals $L^5$ are furthermore eg. methylthio, ethylthio, propylthio, isopropylthio or butylthio.

The radicals $L^1$, $L^2$ and $L^3$ are furthermore eg. formylamino, acetylamino, propionylamino, butyrylamino, isobutyrylamino, methylsulfonylamino, ethylsulfonylamino, propylsulfonylamino, isopropylsulfonylamino or butylsulfonylamino.

The radicals $L^6$ are eg. isoocctyl, 2-ethylhexyl, nonyl, isononyl, decyl, isodecyl, undecyl, dodecyl, tridecyl, isotridecyl, 2- or 4-butoxybutyl, 4,8-dioxadecyl, 3,6,9-trioxaundecyl, 3,6,9,12-tetraoxatridecyl or 3,6,9,12-tetraoxatetradecyl.

Azo dyestuffs of the formula I are preferred where $R^2$ is hydroxyl.

Azo dyestuffs of the formula I are furthermore preferred where $R^1$ is $C_1$–$C_{10}$-alkyl, in particular $C_1$–$C_8$-alkyl.

If D in formula I is a radical of the formula

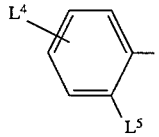

those dyestuffs are preferred where the substituents $L^4$ and $L^5$ have the following arrangement

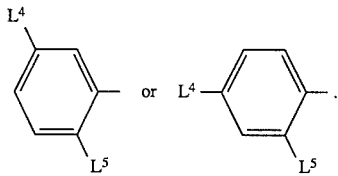

The novel azo dyestuffs of the formula I can be prepared by methods known per se. For example, a diazo component of the formula III

D-NH$_2$          (III)

where D has the abovementioned meaning, can be diazotized in a manner known per se and coupled with a triazolopyridine of the formula IV

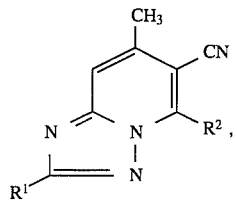

where $R^1$ and $R^2$ in each case have the abovementioned meanings.

The triazolopyridines of the formula IV ($R^2$=hydroxyl) are compounds known per se. They are described eg. in U.S. Pat. No. 5,101,028.

It is a further object of the present invention to make available mercaptotriazolopyridines of the formula II

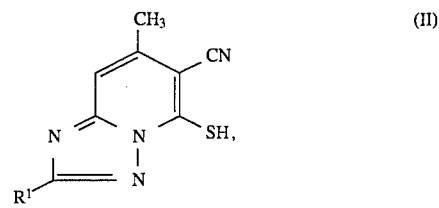

where $R^1$ is $C_1$–$C_{20}$-alkyl which is unsubstituted or substituted and can be interrupted by 1 to 4 ether oxygen atoms, or is unsubstituted or substituted phenyl.

Preferred mercaptotriazolopyridines of the formula II are those where $R^1$ is $C_1$–$C_{10}$-alkyl, in particular $C_1$–$C_8$-alkyl.

The novel mercaptotriazolopyridines of the formula II can be obtained eg. by treating halotriazolopyridines of the formula V

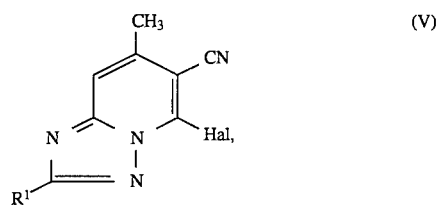

where Hal is chlorine or bromine and $R^1$ has the abovementioned meanings, with hydrogen sulfide. The halotriazolopyridines of the formula V are likewise disclosed in U.S. Pat. No. 5,101,028.

The mercaptotriazolopyridines of the formula II according to the invention are useful intermediates for preparing azo dyestuffs, in particular those of the formula I.

The azo dyestuffs of the formula I according to the invention are advantageously suitable for dyeing or printing textile materials. These are, for example, fibers or fabric composed of cellulose esters or polyesters, but also of polyamides or mixtures of polyesters and cellulose fibers. Dyeings or prints having high fastness to dry heat or pleating and high brilliance are obtained here. The novel dyestuffs also have a high dyeing power.

To achieve a favorable dye composition, it can be advantageous in some cases to use mixtures of the dyestuffs of the formula I with one another for dyeing.

The azo dyestuffs according to the invention are furthermore advantageously suitable for thermal transfer from a support to a plastic-coated paper by means of an energy source (see eg. U.S. Pat. No. 5,079,365).

The following examples will illustrate the invention in greater detail.

EXAMPLE 1 a) Diazotization 4.00 g (0.02 mol) of 2-butoxy-5-methylaniline were dissolved in 80 ml of glacial acetic acid/propionic acid (3:1 v/v) and 16 ml of 85% strength by weight sulfuric acid. At a maximum of from –5° C. to 0° C., 10.4 g of nitrosylsulfuric acid (about 42% by weight $N_2O_3$) were added dropwise. The mixture was then stirred at a maximum of 0° C. for 2 h.

b) Coupling 5.40 g (0.022 mol) of 6-cyano-2-(1'-ethylpropyl)-7-hydroxy-5-methyl[1,2,4]triazolo[1,5-a]pyridine were dissolved in 90 ml of N-methylpyrrolidone and 100 ml of water, 0.5 g of sulfamic acid and about 400 g of ice were added. The diazonium salt solution described in a) was added in portions, the pH being adjusted to from 6.5 to 7.0 using 25% strength by weight sodium hydroxide solution.

The mixture was then stirred at from 0° to 5° C. for 3 h. After coupling was complete, the dyestuff was filtered off with suction at 60° C., washed until neutral and dried under reduced pressure at 60° C. 5.20 g (64% of theory) of the dyestuff of the formula

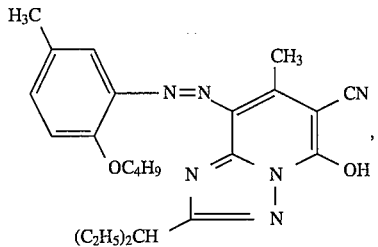

(M.p.: 225°–228° C.; $\lambda_{max}$ (CH$_2$Cl$_2$): 508 nm) were obtained, which dyes polyester in a red shade.

EXAMPLE 2 a) Diazotization 3.90 g (0.025 mol) of 2,4-dimethoxyaniline were introduced at from 0° to 5° C. into a mixture of 20 ml of water, 7.5 g of 35% strength by weight of hydrochloric acid and 15 g of ice. 8 g of 23% strength by weight aqueous sodium nitrite solution were added dropwise at from 0° to 5° C. and the mixture was stirred at from 0° to 5° C. for 3 h.

b) Coupling 6.40 g (0.026 mol) of 5-cyano-2-(1'-ethylpropyl)-7-hydroxy-5-methyl[1,2,4]triazolo[1,5-a]pyridine were dissolved in a mixture of 20 ml of N-methylpyrrolidone, 30 g of ice, 4 g of 50% strength by weight sodium hydroxide solution and 2 g of sodium hydrogencarbonate. After adding 100 g of ice, the diazonium salt solution described in a) was added in the course of 10 min and the mixture was then stirred at 5° C. for 5 h. After coupling was complete, the dyestuff was filtered off with suction at 60° C., washed with water at 60° C. until neutral and dried at 60° C. under reduced pressure. 5 g (49% of theory) of the dyestuff of the formula

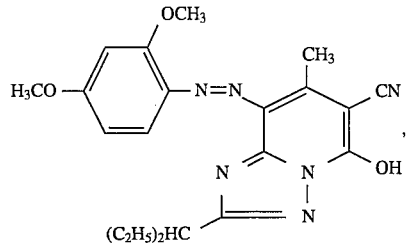

(M.p.: >230° C.; $\lambda_{max}$ (CH$_2$Cl$_2$): 514 nm) were obtained, which dyes polyester in a red shade.

The dyestuffs listed in the following table can be obtained in a similar manner.

TABLE

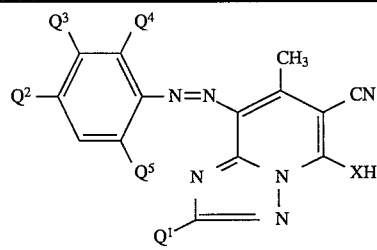

| Ex. No. | X | $Q^1$ | $Q^2$ | $Q^3$ | $Q^4$ | $Q^5$ | M.p. [°C.] | $\lambda_{max}$ [nm] in CH$_2$Cl$_2$ | Color shade on polyester |
|---|---|---|---|---|---|---|---|---|---|
| 3 | O | C$_3$H$_7$ | CH$_3$O | H | CH$_3$ | H | 255–256 | | Yellowish-red |
| 4 | O | C$_3$H$_7$ | CH$_3$ | H | CH$_3$O | H | 237–238 | | Yellowish-red |
| 5 | O | C$_3$H$_7$ | CH$_3$ | CH$_3$O | H | H | 206–207 | 508 | Red |
| 6 | O | CH(C$_2$H$_5$)C$_4$H$_9$ | CH$_3$O | H | CH$_3$O | H | 210 | 515 | Bluish-red |
| 7 | O | C$_4$H$_9$ | CH$_3$O | H | CH$_3$O | H | 235–237 | 516 | Bluish-red |
| 8 | O | CH(C$_2$H$_5$)C$_4$H$_9$ | H | CH$_3$ | H | OC$_2$H$_4$OC$_2$H$_5$ | 159 | 504 | Red |
| 9 | O | CH(C$_2$H$_5$)C$_4$H$_9$ | H | CH$_3$ | H | OC$_4$H$_9$ | 203–206 | 508 | Red |
| 10 | O | C$_4$H$_9$ | H | CH$_3$ | H | OC$_4$H$_9$ | 200–204 | 508 | Red |
| 11 | O | C$_3$H$_7$ | H | CH$_3$ | H | OC$_4$H$_9$ | 215–220 | 508 | Red |
| 12 | O | C$_3$H$_7$ | H | CH$_3$ | H | OC$_2$H$_4$OC$_2$H$_5$ | 200–201 | 504 | Red |
| 13 | O | C$_4$H$_9$ | H | CH$_3$ | H | OC$_2$H$_4$OC$_2$H$_5$ | 188–189 | 504 | Red |
| 14 | S | CH(C$_2$H$_5$)C$_4$H$_9$ | CH$_3$O | H | CH$_3$O | H | >230 | 508 | Red |
| 15 | S | CH(C$_2$H$_5$)C$_4$H$_9$ | H | CH$_3$ | H | OC$_4$H$_9$ | 209–212 | 514 | Red |
| 16 | S | CH(C$_2$H$_5$)C$_4$H$_9$ | H | CH$_3$ | H | OC$_2$H$_4$OC$_2$H$_5$ | 148–153 | 504 | Red |
| 17 | O | C$_4$H$_9$ | H | H | H | SC$_4$H$_9$ | 180–185 | 468 | Yellow |
| 18 | O | C$_3$H$_7$ | CH$_3$ | CH$_3$ | H | H | 252–253 | 476 | Reddish-yellow |
| 19 | O | C$_3$H$_7$ | C$_{12}$H$_{25}$ | H | H | H | 144–145 | 474 | Reddish-yellow |
| 20 | O | C$_3$H$_7$ | OC$_6$H$_5$ | H | H | H | 196–197 | 482 | Orange |
| 21 | O | CH(C$_2$H$_5$)C$_4$H$_9$ | OC$_6$H$_5$ | H | H | H | 163–164 | 482 | Orange |
| 22 | O | C$_3$H$_7$ | H | H | H | OC$_2$H$_5$ | 210–212 | 488 | Orange |

EXAMPLE 23

Gaseous hydrogen sulfide was added with ice-cooling for 1 h to a mixture of 300 ml of 1-methoxy-propan-2-ol and 25 g of triethylamine. 58 g of the compound of the formula

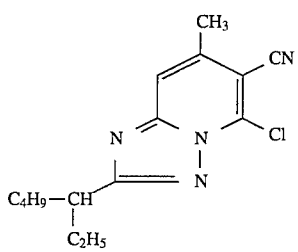

were then added and gaseous hydrogen sulfide was passed in for a further 4 h. The resulting reaction mixture was poured onto 18% strength by weight hydrochloric acid, a precipitate being formed. This was filtered off with suction, washed with water and dried at 80° C. under reduced pressure. 51 g of the compound of the formula

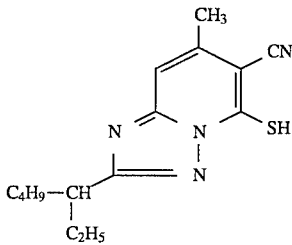

were obtained.

Melting point (from N,N-dimethylformamide/acetic acid): 270°–271° C.; Analysis: $C_{15}H_{20}N_4S$ (288), Calc.: C 62.5 H 7.0 N 19.4 S 11.1, Found: C 62.5 H 7.0 N 19.4 S 10.8.

We claim:

1. An azo dyestuff of the formula I

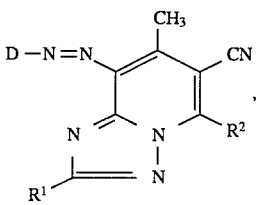

where $R^1$ is $C_1$–$C_{20}$-alkyl which is unsubstituted or substituted and can be interrupted by 1 to 4 ether oxygen atoms, or is unsubstituted or substituted phenyl, or mercapto or unsubstituted or substituted alkylthio, $R^2$ is hydroxyl or mercapto and D is the radical of a diazo component which is selected from the group consisting of the radicals of the formulae

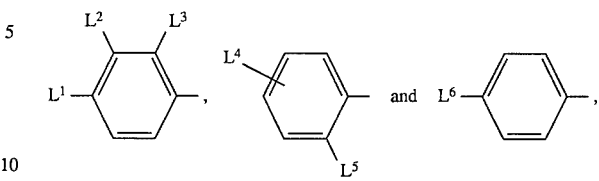

where $L^1$ is $C_1$–$C_4$-alkyl, $C_1$–$C_4$-alkoxy which is unsubstituted or substituted by $C_1$–$C_4$-alkoxy, or is $C_1$–$C_4$-alkanoylamino, $C_1$–$C_4$-alkylsulfonylamino or a radical of the formula $NY^1Y^2$, where $Y^1$ and $Y^2$ independently of one another in each case are hydrogen or $C_1$–$C_4$-alkyl or, together with the nitrogen bonding them, are a 5- or 6-membered saturated heterocyclic radical, one of the two radicals $L^2$ and $L^3$ is hydrogen and the other is $C_1$–$C_4$-alkyl, $C_1$–$C_4$-alkoxy which is unsubstituted or substituted by $C_1$–$C_4$-alkoxy, or is $C_1$–$C_4$-alkanoylamino, $C_1$–$C_4$-alkylsulfonylamino or a radical of the formula $NY^1Y^2$, in which $Y^1$ and $Y^2$ in each case have the above-mentioned meanings, $L^4$ is hydrogen or $C_1$–$C_4$-alkyl, $L^5$ is $C_1$–$C_4$-alkoxy which is unsubstituted or substituted by $C_1$–$C_4$-alkoxy, or is $C_1$–$C_4$-alkylthio and $L^6$ is $C_8$–$C_{13}$-alkyl which can be interrupted by 1 to 4 ether oxygen atoms, or is phenoxy.

2. An azo dyestuff as claimed in claim 1, wherein $R^2$ is hydroxyl.

3. An azo dyestuff as claimed in claim 1, wherein $R^1$ is $C_1$–$C_{10}$-alkyl.

4. A process for dyeing or printing a textile material comprising applying an azo dyestuff of claim 1 to said textile material.

5. A mercaptotriazolopyridine of the formula II

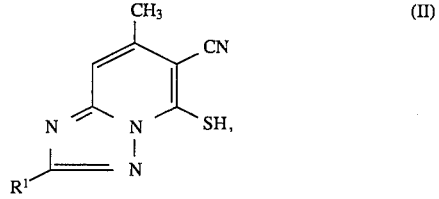

where $R^1$ is $C_1$–$C_{20}$-alkyl which is unsubstituted or substituted and can be interrupted by 1 to 4 ether oxygen atoms, or is unsubstituted or substituted phenyl.

* * * * *